United States Patent
Cabana

(10) Patent No.: US 6,766,532 B1
(45) Date of Patent: Jul. 27, 2004

(54) ADJUSTABLE BACK SUPPORT BELT BRACE SYSTEM AND REMOVABLE, ADJUSTABLE SUSPENSION SYSTEM

(75) Inventor: Daniel F. Cabana, Garden Ridge, TX (US)

(73) Assignee: Rooster Products International, Inc., San Antonio, TX (US)

( * ) Notice: Subject to any disclaimer, the term of this patent is extended or adjusted under 35 U.S.C. 154(b) by 0 days.

(21) Appl. No.: 10/734,454

(22) Filed: Dec. 12, 2003

(51) Int. Cl.[7] ................................................ A61F 5/02
(52) U.S. Cl. .................................. 2/44; 2/310; 602/19
(58) Field of Search ............................... 2/311–312, 44, 2/45, 338, 467, 455, 310, 920; 128/95.1, 96.1, 99.1, 100.1, 846, 869, 875, 876, 845; 602/5, 19, 60–61, 23

(56) References Cited

U.S. PATENT DOCUMENTS

| | | | |
|---|---|---|---|
| 5,040,524 A | * 8/1991 | Votel et al. | 602/19 |
| 5,176,131 A | * 1/1993 | Votel et al. | 602/19 |
| 5,188,586 A | * 2/1993 | Castel et al. | 602/19 |
| 5,257,419 A | * 11/1993 | Alexander | 2/44 |
| 5,349,706 A | * 9/1994 | Keer | 2/300 |
| 5,388,274 A | * 2/1995 | Glover et al. | 2/338 |
| 5,399,151 A | * 3/1995 | Smith | 602/19 |
| 5,484,395 A | * 1/1996 | DeRoche | 602/19 |
| 5,497,923 A | * 3/1996 | Pearson et al. | 224/639 |
| 5,499,965 A | * 3/1996 | Sanchez | 602/19 |
| 5,503,620 A | * 4/1996 | Danzger | 602/19 |
| 5,548,843 A | * 8/1996 | Chase et al. | 2/102 |
| 5,551,085 A | * 9/1996 | Leighton | 2/44 |
| 5,560,046 A | * 10/1996 | Iwamasa et al. | 2/328 |
| 5,656,020 A | * 8/1997 | Greengarg | 602/19 |
| 5,765,224 A | * 6/1998 | Johnson | 2/44 |
| 5,776,087 A | * 7/1998 | Nelson et al. | 602/19 |
| 6,068,606 A | * 5/2000 | Castel et al. | 602/19 |
| 6,137,675 A | * 10/2000 | Perkins | 361/679 |

* cited by examiner

Primary Examiner—Tejash Patel
(74) Attorney, Agent, or Firm—Michelle Evans; Gunn & Lee, P.C.

(57) ABSTRACT

The present invention contains a back support belt brace system comprised of a back panel, two side panels, two side wings, and a belt. The side wings are attached anywhere along the back panel and side panels using a hook and loop fastener providing adjustability. The belt is connected to the back panel, side panels, and two side wings with a hook and loop fastener. The belt contains an end with a belt buckle and an end with a plurality of holes, which are interlocked to secure the brace. An adjustable suspension system is attached to the support brace using clips. The suspension system contains adjustable suspenders, shoulder padding, and upper back padding. The back support belt brace system is worn around the waist and the lumbar region of a wearer. The suspension system is worn around the chest and upper back of a wearer, similar to a vest.

27 Claims, 6 Drawing Sheets

ADJUSTABLE BACK SUPPORT BELT BRACE SYSTEM AND REMOVABLE, ADJUSTABLE SUSPENSION SYSTEM

BACKGROUND OF THE INVENTION

1. Field of the Invention

The present invention relates generally to the field of back support belts and, more specifically, to a back support belt brace with adjustable side wings and belt and with removable and adjustable suspenders.

2. Description of Related Prior Art

Many occupations require strenuous use of back muscles such as heavy lifting by construction workers, fire fighters, and delivery personnel. Therefore, there are many back injuries, particularly lower back injuries, due to excessive strain on the back. This causes extensive lost work and often chronic lower back pain. There are a wide variety of back support belts to help reduce back injuries.

Numerous belts have been patented for back support, which contain back and side panels (some of which are elastic) with additional tensioning pulls to adjust the belt or merely a normal belt with buckle. Most of these patents provide levels of adjustability through the elastic tension pulls. A shortfall of elastic tension pulls or elastic back and/or side panels is they wear out fairly quickly, and it is often hard to comfortably adjust the tightness of the belt. The present invention provides adjustability through a different mechanism. The present invention has two side wings to allow the brace to be adjusted by moving the side wings and reconnecting with the Velcro fastener to the brace. Also, there is a belt that wraps around and connects to the entire brace and provides another level of adjustability using a belt buckle.

Many support belts do not contain any suspenders. A shortcoming of this is that during breaks from lifting, the support belt must be totally removed. Some patented belts do have removable adjustable suspenders; however, they are all similar to normal pant suspenders. Normal pant suspenders do not provide enough support to the brace. The present invention provides more comfortable, durable, and supportive suspenders with padding on both shoulders and upper back.

U.S. Pat. Nos. 5,040,524 and 5,176,131, both to Vogel et al., disclose a Back Support. The back support has two panels that connect together in the front of the wearer with hook and loop fasteners. The back panel has semi-rigid stays. Two elastic bands are connected to the back panel and are pulled towards the front of the wearer and hook to the side panels. A belt is passed through loops on the panels, which connects in the front with a buckle. Adjustable suspenders with small shoulder pads are attached to each side panel in the front of the wearer and cross in the back to attach in two locations on the back panel.

U.S. Pat. Nos. 5,188,586 and 6,068,606, both to Castel et al., disclose a Back Support Belt. The back support belt has right and left side panels which are connected with a back elastic panel. The front of the support is connected with a fastening material. Rigid vertical stays are connected to the back panel. The snugness of the support is adjusted by the position of tensioning pulls connected to the back elastic panel. Adjustable suspenders are attached to each side panel in the front of the wearer and cross in the back to attach in two locations on the back panel. A wearer's normal belt for holding up his/her pants is connected through loops onto the inside of the support.

U.S. Pat. No. 5,257,419 to Alexander discloses an Abdominal Support Belt. The abdominal support belt has two side panels and a back support with longitudinal corset stays. The side panels connect in the front of the wearer with a hook and loop material at different positions depending on the size of the wearer's waist. Tensioning straps, which are made of elastic, are connected to the waistband and are pulled to provide enhanced support to the abdomen and back. Adjustable suspenders are attached to each side panel in the front of the wearer and cross in the back to attach in two locations on the back panel.

U.S. Pat. No. 5,349,706 to Keer discloses Work Belts with Lumbar Supports, Stretchable Side Panels and Interchangeable Pouches. The work belts have elastic side panels on the lumbar support with interchangeable pouches or pockets. The side panels connect like a belt with a buckle on one end and holes on the other end. Adjustable suspenders are attached to each side panel in the front of the wearer and cross in the back to attach in two locations on the back panel.

U.S. Pat. No. 5,497,923 to Pearson et al. discloses a Suspender Supported Belt. The suspender support belt has two side panels and an elastic back panel. The side panels connect in the front of the wearer. An elastic belt is connected to the back support belt for attachment of secure pouches and hook and loop fasteners for tools. Adjustable suspenders are attached to each side panel in the front of the wearer and cross in the back to attach in two locations on the back panel.

U.S. Pat. No. 5,499,965 to Sanchez discloses a Shaped Lifting Belt and Method. The shaped lifting belt has a lumbar panel, two shape panels, and two side panels. Vertical stays are on the lumbar panel. Shape straps are connected on both sides of the lumbar panel to shape the shape panels to fit the hips of the wearer. On top of the shape straps are side pulls, which are pulled and connected onto the side panels. The side panels connect with loop and hook surfaces in the front of the wearer. Adjustable suspenders are attached to each side panel in the front of the wearer and cross in the back to attach in two locations on the back panel.

U.S. Pat. No. 5,503,620 to Danzger discloses a Back Support Belt Apparatus and Method. The back support belt apparatus has a primary support belt that fits around the waist of the wearer. The ends of the primary support belt connect in the front of wearer. There is a secondary tensioning belt of a smaller width connected to the primary support belt. The belt also contains tensioning indicators of dangercolored strips to indicate to the wearer and/or observer if the belt is not tightened enough to provide proper support to the abdominal and lumbar areas. Adjustable suspenders are attached to each side panel in the front of the wearer and cross in the back to attach in two locations on the back panel.

U.S. Pat. No. 5,548,843 to Chase et al. discloses a Back Support with Means to Secure the Belt on the Wearer while in an Open Position. The back support has a primary belt with a back support with left and right side panels. The side panels connect in the front of the wearer with hook and pile fasteners. A secondary belt is connected to the suspenders through loops on the secondary belt. Two cinch straps made of elastic material are connected to the back support and wrap around the primary belt and connect in the front of the wearer with hook and pile fasteners. Adjustable suspenders are attached to each side panel in the front of the wearer and cross in the back to attach in two locations on the back panel.

U.S. Pat. No. 5,560,046 to Iwamasa et al. discloses a Lumbar Support Belt with Suspenders and Elastic Sections Having Different Elasticities. The lumbar support belt has a back elastic panel and two side panels. The side panels connect in the front of the wearer with hook and pile fasteners. Elastic strips are connected to the back panel and are pulled and connected to the side panels to adjust to the size of the wearer. Adjustable suspenders are attached to each side panel in the front of the wearer and cross in the back to attach in two locations on the back panel.

U.S. Pat. No. 5,656,020 to Greengarg discloses a Lifting Belt, Panel and Method. The belt has a lifting belt with back elastic panel and two side panels. The back panel extension to the upper back forms into an apron and is detachable and disposable. Detachable elastic bands connect to the back panel and wrap around to the side panels and connect with loop and hook fasteners. Adjustable suspenders are attached to each side panel in the front of the wearer and cross in the back to attach in two locations on the back panel.

U.S. Pat. No. 5,765,224 to Johnson discloses a Body Support Garment. The body support garment has waist shaped fabric garment panels that wrap around the front, back, and side torso in an hourglass shape. The ends of the garment connect in the front of the wearer with hook and pile attachment. The garment is stretchable except the back panel, which is more rigid. There is an auxiliary elastic-type wrap band connected to the back panel that wraps around to the side where it connects to the side panels with hook and pile fastener in the position to provide enhanced support. Adjustable shoulder straps are connected to the side panels and extend over the shoulders to a vertical back panel connected to the back panel of the support.

U.S. Pat. No. 5,766,087 to Nelson et al. discloses a Back Brace. The back brace has a waist belt with a non-elastic back portion and elastic side panels. The side panels connect in the front of the wearer with a hook and loop fastener. Two side pulls are connected to the back portion and can be connected in different positions on the belt. Adjustable suspenders are attached to each side panel in the front of the wearer and cross in the back to attach in two locations on the back panel.

SUMMARY OF THE INVENTION

Generally, the present invention contains a back support belt brace system consisting of a back panel, two side panels, two side wings, and a belt. The side wings are attached anywhere along the back panel and side panels using a hook and loop fastener. This allows any wearer to adjust the size of the system depending on their body size. The belt is connected to the back panel, side panels, and two side wings with a hook and loop fastener. The belt contains an end with a belt buckle and an end with a plurality of holes, which are interlocked to secure the brace when buckled. An adjustable suspension system is attached to the support brace using clips. The suspension system contains adjustable suspenders, shoulder padding, and upper back padding. The back support belt brace system is worn around the waist and the lumbar region of a wearer. The suspension system is worn around the chest and upper back of a wearer, similar to a vest.

In view of the foregoing, the principal object of the present invention is to provide an improved adjustable back brace to support and stabilize the lumbar region of the spine.

It is another object of the present invention to provide a support that reduces the occurrence of back injuries and chronic back pain.

It is another object of the present invention to provide two components of adjustability in the supporting brace system. This is provided with side wings that may be positioned along each part of the support brace depending on the size of the wearer. This is also provided by the belt buckle that secures closed the support brace system.

It is another object of the present invention to provide another component of adjustability in the removable suspension system. This is provided with the adjustability of the suspenders.

It is another object of the present invention to provide a convenient back support and suspension system with a belt to allow a secured position while lifting and an unsecured position during breaks. This allows a wearer to keep the entire system on during breaks and not have to take off the entire system every time the wearer is not lifting something.

It is another object of the present invention to provide a support brace and suspension system that can be worn over any type of work clothes and/or worn under a heavy coat.

It is another object of the present invention to provide a fairly lightweight support brace and suspension system for comfort while working.

It is another object of the present invention to provide a durable support brace and suspension system that will not wear out quickly.

It is another object of the present invention to provide a back support belt brace system that can be conveniently used to attach items thereto, such as tools.

It is another object of the present invention to provide an inexpensive back brace and suspension system for any occupation.

These and other objects and advantages of the present invention will become apparent to one skilled in the art from the detailed description of the invention and the claims, with it understood that other configurations or substitutions of material may be used and are included within the scope of the claims of this invention.

BRIEF DESCRIPTION OF THE DRAWINGS

Details of this invention are described in connection with the accompanying drawings.

DETAILED DESCRIPTION OF THE PREFERRED EMBODIMENT

Figure 1:
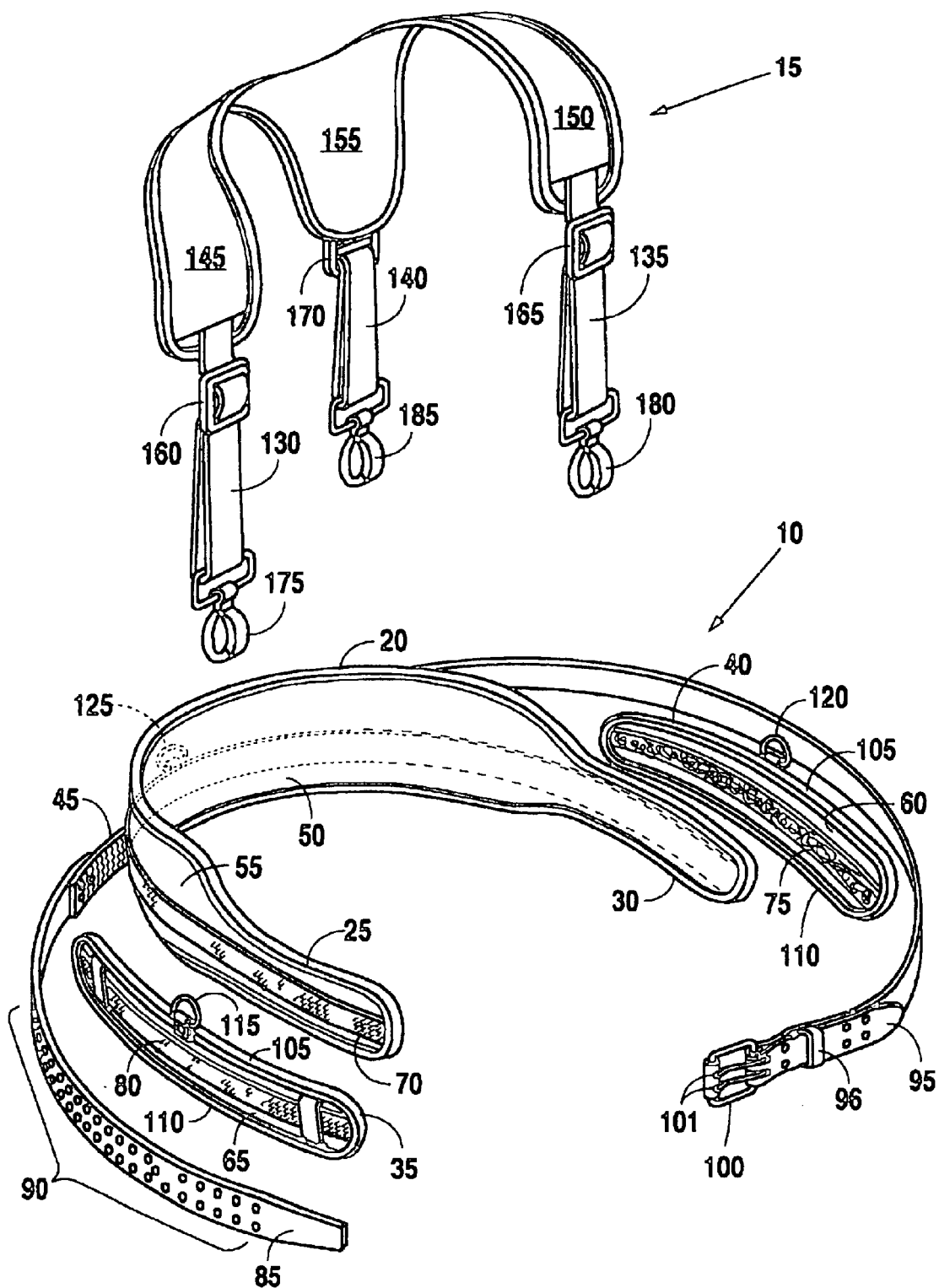
FIG. 1 is an exploded view of the back support belt brace system and removable suspension system.

Referring to FIG. 1, there are two major components of the present invention. The invention includes an adjustable back support belt brace system 10 and a removable, adjustable suspension system 15. The back support belt brace system 10 contains six components including a back panel 20, two side panels 25, 30, two side wings 35, 40, and a belt 45. Back panel 20, side panels 25, 30, and side wings 35, 40 are preferably made of a durable, woven material with inner padding. Belt 45 is preferably made of a durable, woven material.

Back panel 20 and side panels 25, 30 have inner surfaces 50 and outer surfaces 55. The inner surfaces 50 are worn against the body of a wearer and outer surfaces 55 are worn facing away from the body of a wearer. A fastener 70 extends around the outer surface 55 of back panel 20 and side panels 25, 30. Fastener 70 is preferably at least the width of belt 45. Fastener 70 is preferably made of a hook and loop fastener material such as VELCRO. The inner surface 50 of back panel 20 and side panels 25, 30 may have a netting type material to protect the material from wear and tear.

Side wings 35, 40 each have inner surfaces 60, outer surfaces 65, upper edges 105, and lower edges 110. A fastener 75 extends the length of side wings 35, 40 on the inner surfaces 60 of each side wing 35, 40. Fastener 75 is preferably at least the width of belt 45 and is preferably placed evenly between the upper edge 105 and lower edge 110 of side wings 35, 40. A fastener 80 extends the length of side wings 35, 40 on the outer surface 65 of each side wing 35, 40. Fastener 80 is preferably at least the width of belt 45 and is preferably placed evenly between the upper edge 105 and lower edge 110 of side wings 35, 40. Fasteners 75, 80 are preferably made of a hook and loop fastener material such as VELCRO.

Belt 45 contains two belt ends 85, 95. Belt end 85 has a plurality of holes 90 and belt end 95 has a belt holder 96, a belt buckle 100, and belt buckle rods 101. Belt 45 is preferably made of a durable, woven material. Belt ends 85, 95 and belt holder 96 are preferably made of a durable, leather material. Belt buckle 100 and belt buckle rods 101 are preferably made of metal.

Side wings 35, 40 contain rings 115, 120, respectively, on the upper edges 105 for connection of the back support belt brace system 10 to the suspension system 15. Back panel 20 contains a ring 125 on the outer surface 55 preferably centrally located between the side panels 25, 30. Rings 115, 120, 125 are preferably made of metal.

Suspension system 15 contains two front suspenders 130, 135 and one back suspender 140. Suspenders 130, 135 are connected to shoulder padding 145, 150, respectively, and back suspender 140 is connected to back padding 155. Adjusters 160, 165, 170 are used to adjust the length of the suspenders 130, 135, 140, respectively, on the suspension system 15. Clips 175, 180 connect to front suspenders 130, 135, respectively, and clip 185 connects to back suspender 140. Clips 175, 180, 185 are preferably made of metal. Clips 175, 180, 185 interlock with rings 115, 120, 125, respectively, to connect the back support belt brace system 10 with the suspension system 15 (see FIGS. 3, 4).

Figure 2:
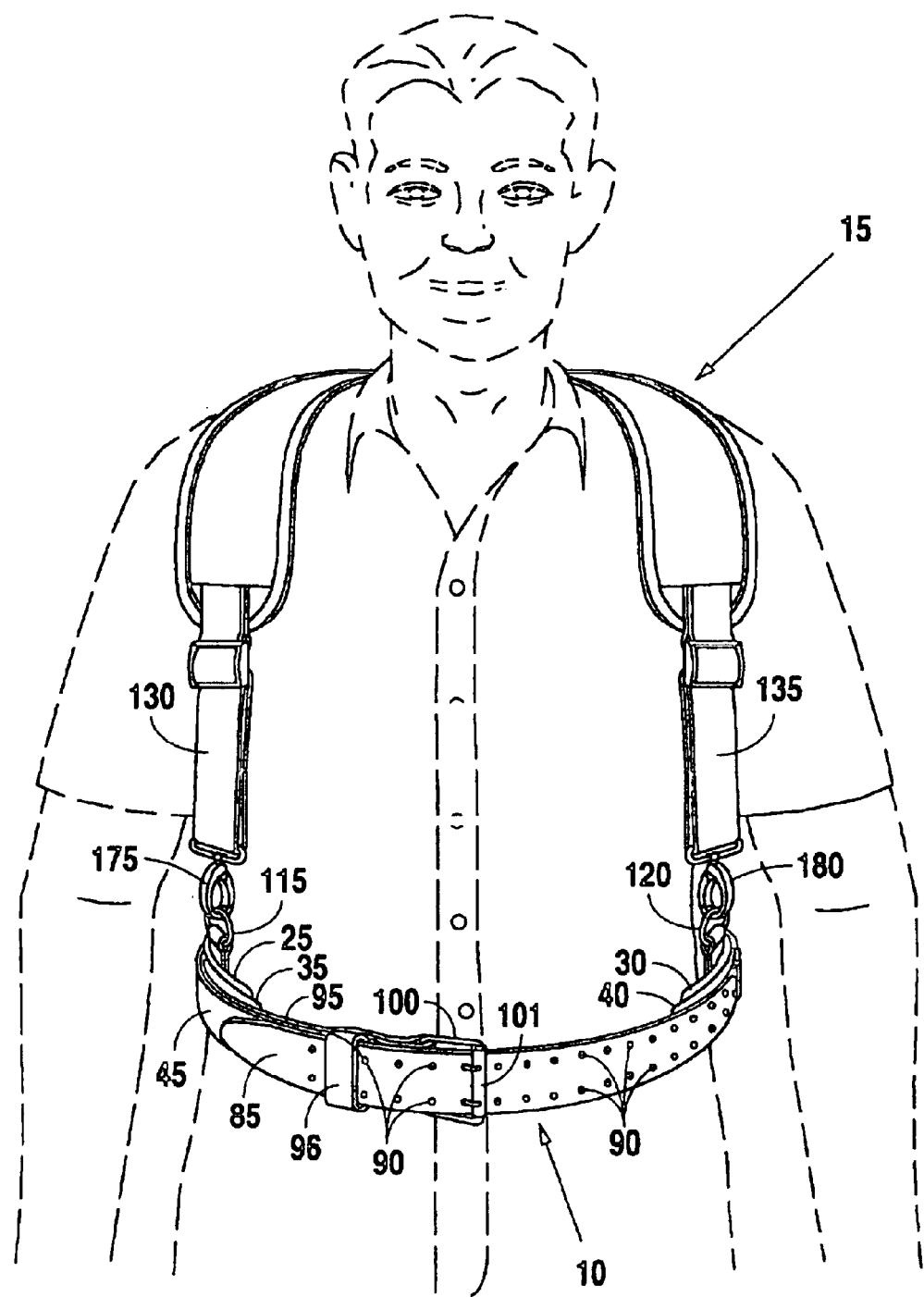
FIG. 2 is a front environmental, perspective view with the back support belt brace system and the removable suspension system secured on a person with the belt closed.

Referring to FIG. 2, the back support belt brace system 10 and adjustable suspension system 15 are illustrated attached together on a wearer with belt 45 in a closed, secured position. The suspension system 15 is attached to the back support belt brace system 10 with rings 115, 120 on side wings 35, 40, respectively, and clips 175, 180 on the suspenders 130, 135, respectively. The connection is also made with ring 125 on the back panel 20 and clip 185 on the back suspender 140 (see FIG. 4). Side wings 35, 40, illustrated in FIG. 1 in a disconnected position, are connected in FIG. 2 to side panels 25, 30 and back panel 20. This connection is made between fasteners 70, 75 and can be in any position along fastener 70 (see FIG. 6). Fastener 70 is preferably a hook fastener, and fastener 75 is preferably a fastener to allow a connection between the two. Belt 45, illustrated in FIG. 1 in a disconnected position, is connected in FIG. 2 to side wings 35, 40, back panel 20, and side panels 25, 30. This connection is made between material of belt 45, fastener 80 on side wings 35, 40 and fastener 70 on back panel 20 and side panels 25, 30. Fastener 80 is preferably a hook fastener to allow connection with belt 45, which is preferably a woven material that can act as a loop fastener with fasteners 70, 80. Belt ends 85, 95 are shown in a secured, closed position created by insertion of belt buckle rods 101 of the belt buckle 100 into any of the plurality of holes 90 and then securing belt end 85 into the belt holder 96.

Figure 3:
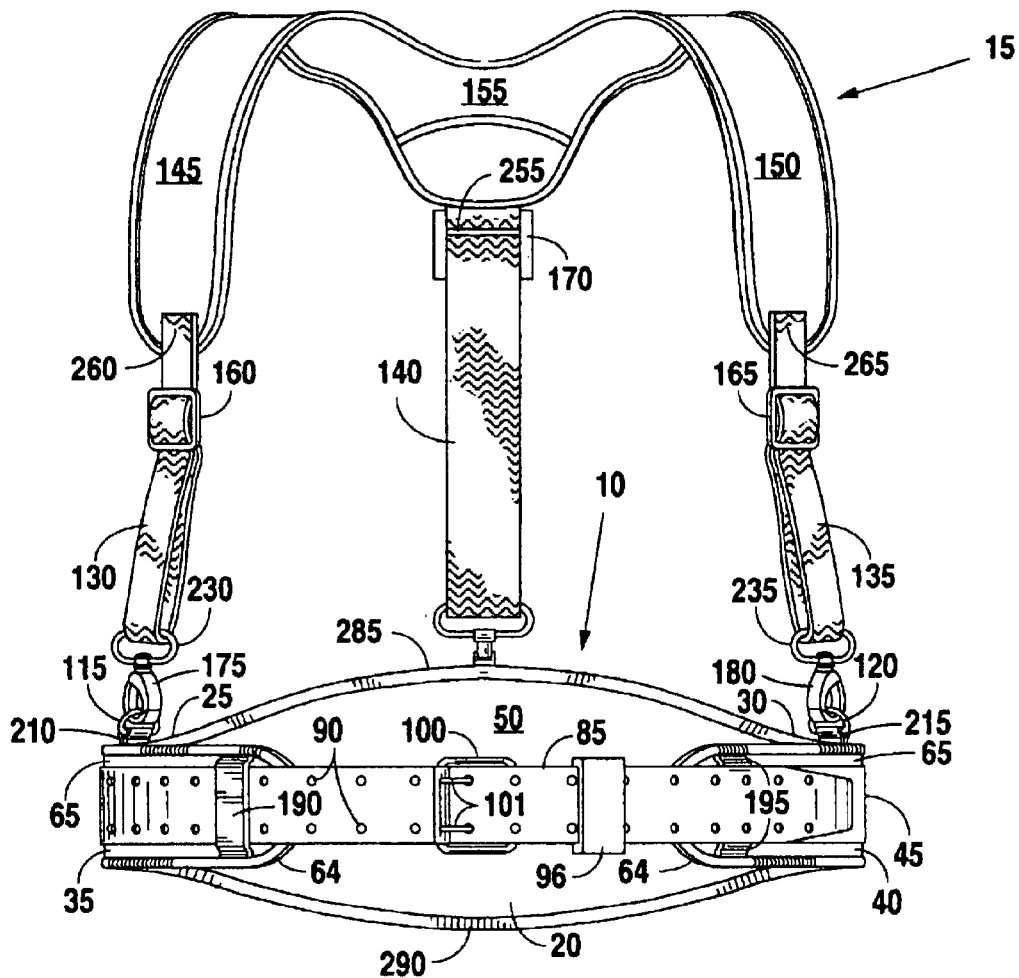
FIG. 3 is a front elevational view of the back support belt brace system and removable suspension system with the belt closed.
Figure 4:
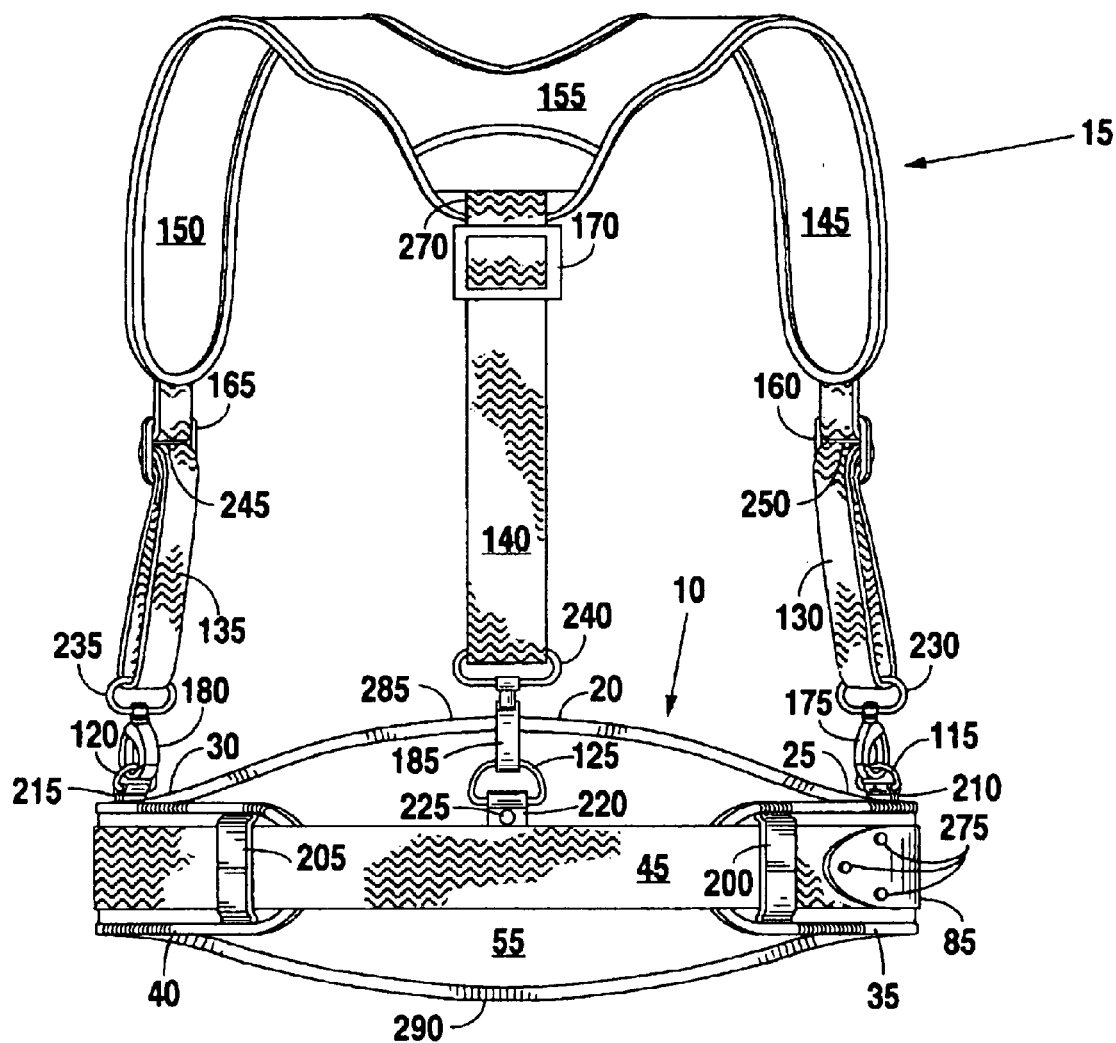
FIG. 4 is a rear elevational view of the back support belt brace system and removable suspension system.

Referring to FIGS. 3, 4, front and back elevational views of the back support belt brace system 10 and suspension system 15 are illustrated connected together as would be worn on a wearer. These views provide more detail views of the components of each system. Back panel 20, side panels 25, 30, side wings 35, 40, and belt 45 are illustrated in their connected position. The inner surface 50 of back panel 20 and side panels 25, 30 and the outer surfaces 65 of side wings 35, 40 are illustrated in FIG. 3. The outer surface 55 of back panel 20 and side panels 25, 30 and the outer surfaces 65 of side wings 35, 40 are illustrated in FIG. 4. The upper edge 285 of back panel 20 is worn facing the upper body of a wearer and lower edge 290 of back panel 20 is worn facing the lower body of a wearer. Back panel 20 is generally oval in shape and contiguous with side panels 25, 30, which are generally long oval shapes. Side wings 35, 40 are generally long oval shape and. preferably longer than side panels 25, 30.

Belt loops 190, 195 are illustrated on side wings 35, 40 extending from the upper edges 105 to the lower edges 110 of side wings 35, 40. Belt 45 is secured to side wings 35, 40 through belt loops 190, 195, 200, 205 (see FIGS. 3, 4). Belt loops 190, 195, 200, 205 are preferably made of a durable, woven material. Belt 45 can be connected to the outer surface 65 of side wings 35, 40 with fastener 80 and material of belt 45 (see FIGS. 1, 6). Belt buckle 100 is connected to belt end 85 using the plurality of holes 90, which connect together by placing belt buckle rods 101 through any of the plurality of holes 90 depending on the size of the wearer. Belt end 85 is then secured within belt holder 96. FIG. 4 illustrates the connection of belt end 85 to belt 45 with connectors 275. Connectors 275 are preferably metal rods.

Rings 115, 120 on side wings 35, 40, respectively, are connected onto the upper edges 105 of side wings 35, 40 with clasps 210, 215, respectively. Clasps 210, 215 are preferably made of a durable, woven material. Connectors 226 are used to secure the clasps to side wings 35, 40 in a loop fashion (see FIG. 5). Connectors 226 are preferably metal rods. Rings 115, 120 are secured in the loops of clasps 210, 215. Ring 125 is connected to back panel 20 with clasp 220. Clasp 220 is preferably made of a durable, woven material. Connector 225 is used to secure the clasp to back panel 20 in a loop fashion (see FIGS. 4, 5). Connector 225 is preferably a metal rod. Ring 125 is secured into the loop of clasp 220.

Suspension system 15 contains two front suspenders 130, 135 and one back suspender 140. Suspenders 130, 135 are connected to shoulder padding 145, 150, respectively, at 260, 265, respectively. Connection 260, 265 is preferably obtained by sewing. Suspender 140 is connected to back padding 155 at 270. Connection 270 is preferably obtained by sewing.

Adjusters 160, 165, 170 are used to adjust the length of the suspenders 130, 135, 140, respectively, on the suspension system 15. Adjusters 160, 165, 170 are preferably made of a plastic material. Each adjuster 160, 165, 170 preferably has top and bottom openings created with plastic rods 245, 250, 255, respectively, across the center of each adjuster 160, 165, 170, respectively (see FIGS. 3, 4). Rods 245, 250, 255 allow the movement of suspenders 130, 135, 140 in varying positions depending on the size of a wearer's upper body.

Clips 175, 180 connect to front suspenders 130, 135, respectively, with rings 230, 235, respectively. Rings 230, 235 connect into the loop of suspenders 130, 135, respectively, formed by insertion of suspenders 130, 135 through adjusters 160, 165. Rings 230, 235 are preferably made of metal. Clip 185 connects to back suspender 140 with ring 240. Ring 240 connects into the loop of suspender 140 formed by insertion of suspender 140 through adjuster 170. Ring 240 is preferably made of metal. Clips 175, 180, 185 interlock with rings 115, 120, 125, respectively, to connect the back support belt brace system 10 with the suspension system 15.

Figure 5:
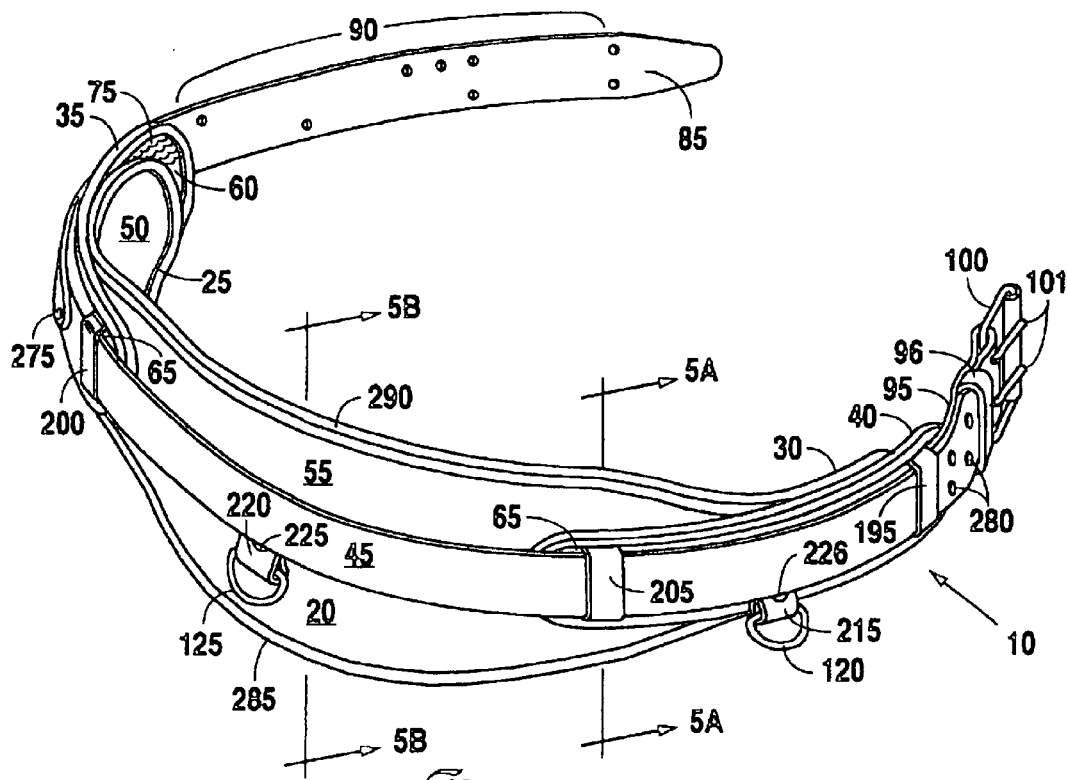
FIG. 5 is a bottom perspective view of the back support belt brace system.
Figure 5A:
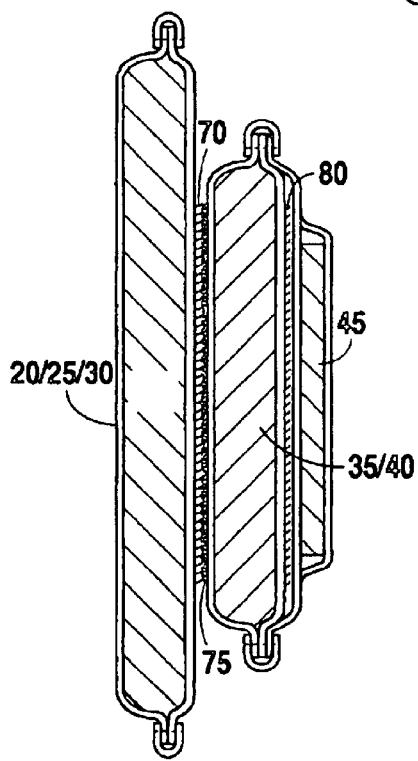
FIG. 5A is a cross sectional view of the back support belt brace system along line 5A—5A in the direction of the arrows of the back support belt brace system in FIG. 5.
Figure 5B:
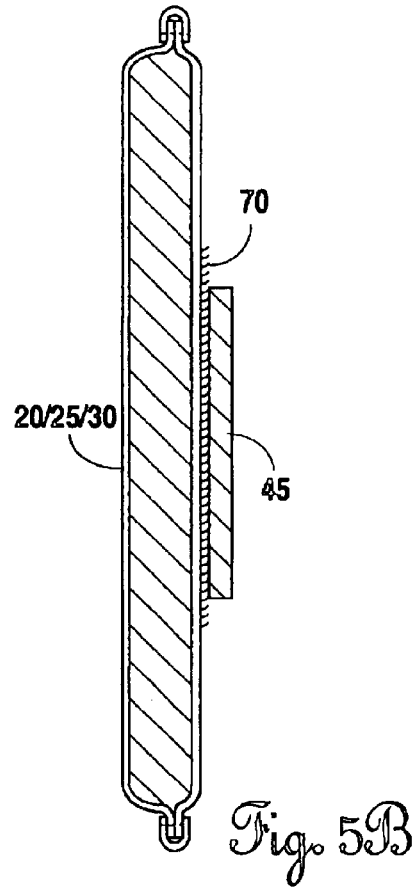
FIG. 5B is a cross sectional view of the back support belt brace system along line 5B—5B in the direction of the arrows of the back support belt brace system in FIG. 5.

Referring to FIG. 5, a bottom perspective view of the back support belt brace system 10 is illustrated to provide additional detail of the adjustability components. The upper edge 285 of back panel 20 is facing downward and lower edge 290 is facing upward in the figure to provide a bottom view. FIG. 5 illustrates the inner surfaces 50 of side panel 25, outer surfaces 55 of back panel 20 and side panels 25, 30, inner surface 60 of side wing 35, and outer surfaces 65 of side wings 35, 40. FIGS. 5A, 5B provide cross-sections for illustration of the adjustability connections.

Outer surface 55 of back panel 20 and side panels 25, 30 have two elements connected to them. First, side wings 35, 40 are connected in any position on side panels 25, 30 and back panel 20. This connection is made with fastener 70 on the outer surfaces 55 of side panels 35, 30 and back panel 20 and fastener 75 on the inner surfaces 60 of side wings 35, 40. The cross section illustrated in FIG. 5A shows this connection. Fastener 70 is illustrated preferably as a hook portion of a hook and loop fastener such as VELCRO. Fastener 75 is illustrated preferably as a loop portion of a hook and loop fastener such as VELCRO. Fasteners 70, 75 interconnect to secure side wings 35, 40 to side panels 25, 30 and back panel 20. Second, belt 45 is connected to back panel 20 using fastener 70 and material of belt 45. The cross section illustrated in FIG. 5B shows this connection. Fastener 70 is illustrated preferably as a hook portion of a hook and loop fastener such as VELCRO. Belt 45 is preferably made of a material that may act as a loop portion of a hook and loop fastener. A larger wearer may have belt 45 also connect to side panels 25, 30 onto fastener 70 because side wings 35, 40 would be placed in a position to allow a larger size back support belt brace system 10 (see FIGS. 5B, 6).

Belt 45 has two belt ends 85, 95. Belt end 85 has a plurality of holes 90 and connects to belt 45 with connectors 275. Belt end 95 has a belt buckle 100, belt buckle rods 101, and belt holder 96. Belt end 95 connects to belt 45 with connectors 280. Connectors 275, 280 are preferably metal rods. Belt end 85 is inserted through belt loops 190, 195, 200, 205 to secure belt 45 to the back support belt brace system 10 (see FIGS. 3, 5). Belt 45 is also secured to side wings 35, 40 with fastener 80 on the outer surface 65 of side wings 35, 40. The cross section illustrated in FIG. 5A shows this connection. Fastener 80 is illustrated preferably as a hook portion of a hook and loop fastener such as VELCRO. Belt 45 is preferably made of a material that may act as a loop portion of a hook and loop fastener. Therefore, material of belt 45 and fastener 80 connect together to secure belt 45 to side wings 35, 40.

Rings 120, 125 used for connection of the back support belt brace system 10 to the suspension system 15 are illustrated in FIG. 5. Ring 120 connects to side wing 40 with clasp 215. Clasp 215 connects to side wings 40 with connector 226. Ring 115 connects to side wing 35 with clasp 210 (see FIGS. 3, 4). Clasp 210 connects to side wing 35 with a similar connector 226 (not illustrated). Ring 125 connects to back panel 20 with clasp 220. Clasp 220 connects to back panel 20 with connector 225.

Figure 6:
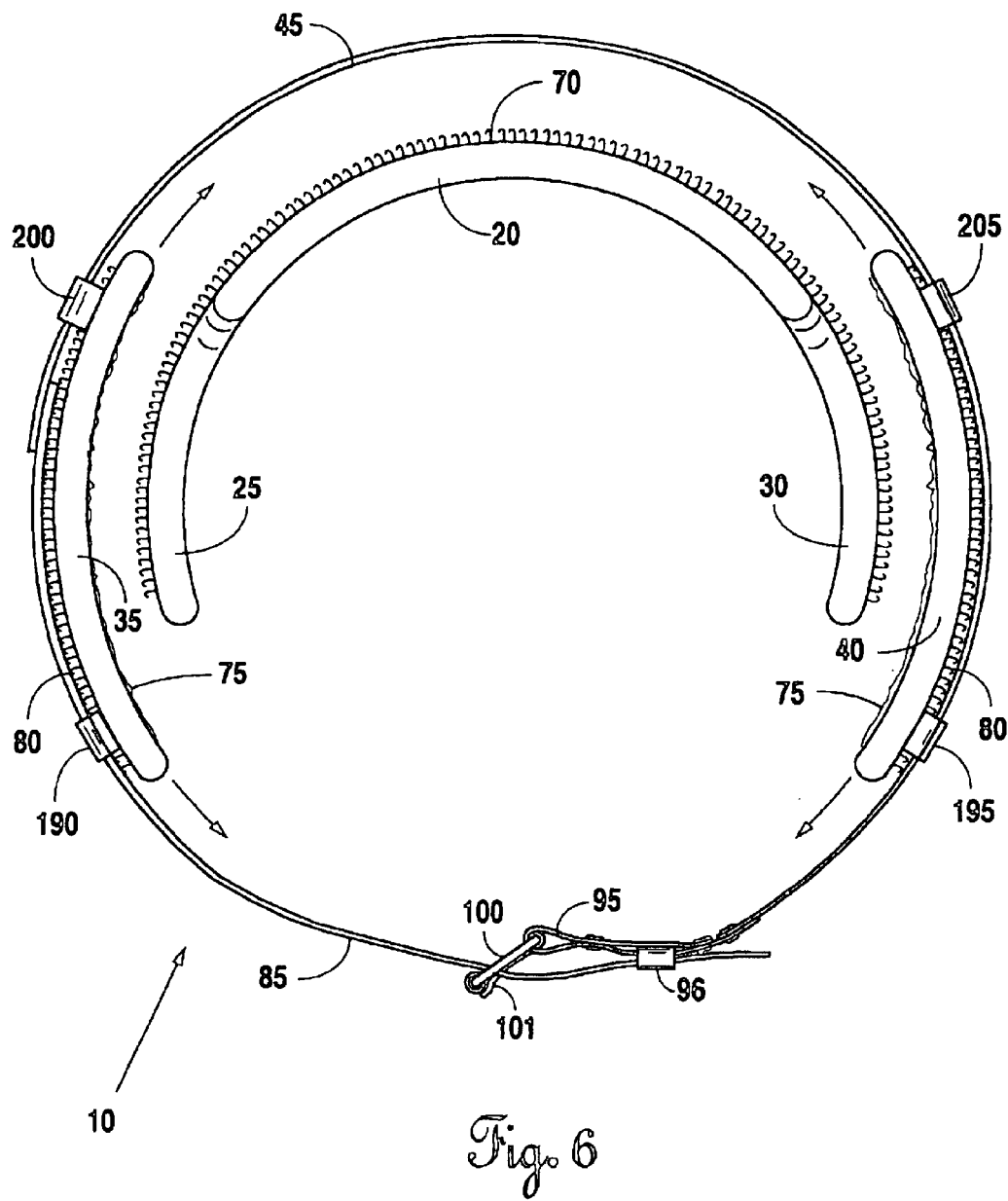
FIG. 6 is top view of the back support belt brace system.

Referring to FIG. 6, a top view of the back support belt brace system 10 is illustrated to further show the adjustability positions of side wings 35, 40. Side wings 35, 40 may be placed anywhere along side panels 25, 30 and/or back panel 20. Side wings 35, 40 connect to side panels 25, 30 and back panel 20 with fastener 75 and fastener 70. The size of the wearer will determine where to place the side wings 35, 40. If a wearer is small, the side wings 35, 40 would be positioned closer to the back panel 20. If a wearer is larger, the side wings 35, 40 would be positioned further away from back panel 20 and likely only on side panels 25, 30. Belt loops 190, 195, 200, 205 along with fastener 80 secure belt 45 to side wings 35, 40. Belt 45 is also secured to back panel 20 and/or side panels 25, 30 depending on the size of the wearer with fastener 70 and material of belt 45. FIG. 6 further illustrates the connection of belt ends 85, 95. Belt buckle 100 connects into belt end 85 with buckle rods 101. Belt end 85 is then secured into belt holder 96.

What is claimed is:

1. An adjustable back support system adaptable for different size wearers to provide support for the lumbar region of the wearer's back while the wearer performs bending or lifting functions comprising:

a back panel for pressing against said lumber region of said wearer's back, said back panel also having side panels that extend to and press against sides of said wearer while in use;

a belt wrapping around and pressing said back panel with said side panels against said wearer while fastened and in use; and side wings insertable between said back panel with said side panels and said belt, said side wings being independently securable and yet moveable with respect to both (1) said belt and (2) said back panel with said side panels.

2. The adjustable back support system adaptable for different size wearers as recited in claim 1 further comprising a suspension system connecting to (1) said back panel with said side panels and (2) said side wings, with a connecting means, said suspension system extending over shoulders of said wearer to maintain vertical position of said back panel against said lumber region of said wearer.

3. The adjustable back support system adaptable for different size wearers as recited in claim 2 wherein said side wings are independently securable and yet movable with respect to both (1) said belt and (2) said back panel with said side panels using hook and loop fasteners.

4. The adjustable back support system adaptable for different size wearers as recited in claim 3 wherein said connecting means between (1) said suspension system (2) said back panel with said side panels and (3) said side wings is a clip on said suspension system and rings on (1) said back panel with said side panels and (2) said side wings.

5. The adjustable back support system adaptable for different size wearers as recited in claim 4 wherein said back panel with said side panels has an outer surface, said side wings have an outer surface and an inner surface, and said hook and loop fasteners are contained on (1) said outer surface of said back panel with said side panels (2) said outer surface of said side wings and (3) said inner surface of said side wings.

6. The adjustable back support system adaptable for different size wearers as recited in claim 5 wherein said belt is constructed of a non-elastic, durable, woven material that acts as a hook and loop fastener.

7. The adjustable back support system adaptable for different size wearers as recited in claim 6 wherein said suspension system contains upper back padding and shoulder padding.

8. The adjustable back support system adaptable for different size wearers as recited in claim 7 wherein said belt contains a belt end with a belt buckle and a belt end with a plurality of holes.

9. The adjustable back support system adaptable for different size wearers as recited in claim 8 wherein said belt ends are constructed of leather and said belt buckle is constructed of metal.

10. The adjustable back support system adaptable for different size wearers as recited in claim 9 wherein said suspension system contains three suspenders with three adjusting means.

11. The adjustable back support system adaptable for different size wearers as recited in claim 10 wherein said back panel with said side panels, said side wings, said upper back padding, and said shoulder padding are constructed of a non-elastic, durable, woven material with inner padding.

12. An adjustable back support system adaptable for different size wearers to provide support for the lumber region of the wearer's back while the wearer performs bending or lifting functions comprising:
    a back panel for pressing against said lumber region of said wearer's back, said back panel also having side panels that extend to and press against sides of said wearer while in use;
    a belt wrapping around and pressing said back panel with said side panels against said wearer while fastened and in use; and
    side wings insertable between said back panel with said side panels and said belt, said side wings being independently securable and yet moveable with respect to both (1) said belt and (2) said back panel with said side panels,
    a suspension system connecting to (1) said back panel with said side panels and (2) said side wings, with a connecting means, said suspension system extending over shoulders of said wearer to maintain vertical position of said back panel against said lumber region of said wearer.

13. The adjustable back support system adaptable for different size wearers as recited in claim 12 wherein said side wings are independently securable and yet movable with respect to both (1) said belt and (2) said back panel with said side panels using hook and loop fasteners.

14. The adjustable back support system adaptable for different size wearers as recited in claim 13 wherein said connecting means between (1) said suspension system (2) said back panel with said side panels and (3) said side wings is a clip on said suspension system and rings on (1) said back panel with said side panels and (2) said side wings.

15. The adjustable back support system adaptable for different size wearers as recited in claim 14 wherein said back panel with said side panels has an outer surface, said side wings have an outer surface and an inner surface, and said hook and loop fasteners are contained on (1) said outer surface of said back panel with said side panels (2) said outer surface of said side wings and (3) said inner surface of said side wings.

16. The adjustable back support system adaptable for different size wearers as recited in claim 15 wherein said belt is constructed of a non-elastic, durable, woven material that acts as a hook and loop fastener.

17. The adjustable back support system adaptable for different size wearers as recited in claim 16 wherein said suspension system contains upper back padding and shoulder padding.

18. The adjustable back support system adaptable for different size wearers as recited in claim 17 wherein said belt contains a belt end with a belt buckle and a belt end with a plurality of holes.

19. The adjustable back support system adaptable for different size wearers as recited in claim 18 wherein said belt ends are constructed of leather and said belt buckle is constructed of metal.

20. The adjustable back support system adaptable for different size wearers as recited in claim 19 wherein said suspension system contains three suspenders with three adjusting means.

21. The adjustable back support system adaptable for different size wearers as recited in claim 20 wherein said back panel with said side panels, said side wings, said upper back padding, and said shoulder padding are constructed of a non-elastic, durable, woven material with inner padding.

22. An adjustable back support system adaptable for different size wearers to provide support for the lumber region of the wearer's back while the wearer performs bending or lifting functions comprising:
    a back panel for pressing against said lumber region of said wearer's back, said back panel also having side panels that extend to and press against sides of said wearer while in use;
    a belt wrapping around and pressing said back panel with said side panels against said wearer while fastened and in use; and
    side wings insertable between said back panel with said side panels and said belt, said side wings being independently securable and yet moveable with respect to both (1) said belt and (2) said back panel with said side panels using hook and loop fasteners,
    a suspension system connecting to (1) said back panel with said side panels and (2) said side wings, with a connecting means, said suspension system extending over shoulders of said wearer to maintain vertical position of said back panel against said lumber region of said wearer, said connecting means is a clip on said suspension system and rings on (1) said back panel with said side panels and (2) said side wings, and said suspension system contains three suspenders with three adjusters, upper back padding, and lower back padding.

23. The adjustable back support system adaptable for different size wearers as recited in claim 22 wherein said back panel with said side panels has an outer surface, said side wings have an outer surface and an inner surface, and said hook and loop fasteners are contained on (1) said outer surface of said back panel with said side panels (2) said outer surface of said side wings and (3) said inner surface of said side wings.

24. The adjustable back support system adaptable for different size wearers as recited in claim 23 wherein said belt is constructed of a non-elastic, durable, woven material that acts as a hook and loop fastener.

25. The adjustable back support system adaptable for different size wearers as recited in claim 24 wherein said belt contains a belt end with a belt buckle and a belt end with a plurality of holes.

26. The adjustable back support system adaptable for different size wearers as recited in claim 25 wherein said belt ends are constructed of leather and said belt buckle is constructed of metal.

27. The adjustable back support system adaptable for different size wearers as recited in claim 26 wherein said back panel with said side panels, said side wings, said upper back padding, and said shoulder padding are constructed of a non-elastic, durable, woven material with inner padding.

* * * * *